United States Patent
Bartsch et al.

(10) Patent No.: US 7,345,006 B2
(45) Date of Patent: Mar. 18, 2008

(54) CATALYST SYSTEM CONTAINING NI(0) FOR HYDROCYANATION

(75) Inventors: Michael Bartsch, Neustadt (DE); Robert Baumann, Mannheim (DE); Dagmar Pascale Kunsmann-Keitel, Limburgerhof (DE); Gerd Haderlein, Darmstadt (DE); Tim Jungkamp, Dossenheim (DE); Marco Altmayer, Mannheim (DE); Wolfgang Siegel, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 497 days.

(21) Appl. No.: 10/484,169

(22) PCT Filed: Jul. 16, 2002

(86) PCT No.: PCT/EP02/07888

§ 371 (c)(1),
(2), (4) Date: Jan. 20, 2004

(87) PCT Pub. No.: WO03/011457

PCT Pub. Date: Feb. 13, 2003

(65) Prior Publication Data

US 2004/0176622 A1    Sep. 9, 2004

(30) Foreign Application Priority Data

Jul. 27, 2001    (DE)    ................. 101 36 488

(51) Int. Cl.
    *B01J 27/185*    (2006.01)
(52) U.S. Cl. .................. 502/213; 558/156; 558/336
(58) Field of Classification Search ............... 558/156, 558/336; 502/213
    See application file for complete search history.

(56) References Cited

U.S. PATENT DOCUMENTS

| | | | |
|---|---|---|---|
| 3,903,120 | A | 9/1975 | Shook, Jr. et al. |
| 5,512,696 | A * | 4/1996 | Kreutzer et al. ............ 558/338 |
| 5,523,453 | A | 6/1996 | Breikss |
| 5,693,843 | A | 12/1997 | Breikss et al. |
| 5,847,191 | A | 12/1998 | Bunel et al. |
| 5,981,772 | A | 11/1999 | Foo et al. |
| 6,127,567 | A | 10/2000 | Garner et al. |
| 6,242,633 | B1 | 6/2001 | Fischer et al. |
| 7,067,685 | B2 * | 6/2006 | Bartsch et al. ............. 556/19 |

FOREIGN PATENT DOCUMENTS

| | | |
|---|---|---|
| WO | 99/64155 | 12/1999 |
| WO | 01/14392 | 3/2001 |

* cited by examiner

*Primary Examiner*—Rei-tsang Shiao
(74) *Attorney, Agent, or Firm*—Novak Druce + Quigg LLP

(57) ABSTRACT

A system comprising
a) Ni(0)
b) from 4 to 10 mol per mol of Ni(0) in a) of a compound (I) of the formula $$P(X^1R^1)(X^2R^2)(X^3R^3) \qquad (I)$$

where
$X^1$, $X^2$, $X^3$ are each, independently of one another, oxygen or a single bond,
$R^1$, $R^2$, $R^3$ are, independently of one another, identical or different organic radicals
and
c) from 1 to 4 mol per mol of Ni(0) in a) of a compound (II) of the formula

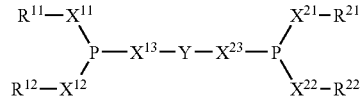

where
$X^{11}$, $X^{12}$, $X^{13}$, $X^{21}$, $X^{22}$, $X^{23}$ are each, independently of one another, oxygen or a single bond,
$R^{11}$, $R^{12}$ are identical or different, individual or bridged organic radicals,
$R^{21}$, $R^{22}$ are identical or different, individual or bridged organic radicals and
Y is a bridging group
is suitable as catalyst for preparing mixtures of monoolefinic $C_5$ mononitriles having nonconjugated C=C and C=N bonds by hydrocyanation of a 1,3-butadiene-containing hydrocarbon mixture and for preparing a dinitrile by hydrocyanation of a mixture of monoolefinic $C_5$ mononitriles having nonconjugated C=C and C=N bonds.

16 Claims, No Drawings

CATALYST SYSTEM CONTAINING NI(0) FOR HYDROCYANATION

This application is a 371 of PCT/EP02/07888 filed on Jul. 16, 2002.

The present invention relates to a system comprising
a) Ni(0)
b) from 4 to 10 mol per mol of Ni(0) in a) of a compound (I) of the formula

where
$X^1, X^2, X^3$ are each, independently of one another, oxygen or a single bond
$R^1, R^2, R^3$ are, independently of one another, identical or different organic radicals
and
c) from 1 to 4 mol per mol of Ni(0) in a) of a compound (II) of the formula

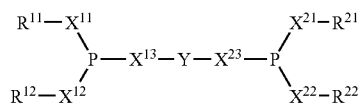

where
$X^{11}, X^{12}, X^{13}, X^{21}, X^{22}, X^{23}$ are each, independently of one another, oxygen or a single bond
$R^{11}, R^{12}$ are identical or different, individual or bridged organic radicals
$R^{21}, R^{22}$ are identical or different, individual or bridged organic radicals and
y is a bridging group which is suitable as catalyst and to processes for preparing such systems.

Systems comprising Ni(0) and a compound (II) which are suitable as catalysts for the hydrocyanation of butadiene to form a mixture of isomeric pentenenitriles and of pentenenitrile to form adiponitrile and processes for preparing them are known per se, for example from U.S. Pat. No. 3,903,120, U.S. Pat. No. 5,523,453, U.S. Pat. No. 5,981,772, U.S. Pat. No. 6,127,567, U.S. Pat. No. 5,693,843, U.S. Pat. No. 5,847,191, WO 01/14392, WO 99/13983 and WO 99/64155.

The preparation of these catalyst systems is technically complicated and expensive. This applies particularly since the catalyst systems are gradually decomposed during use and thus have to be discharged and replaced by fresh catalyst.

The direct reaction of metallic nickel as Ni(0) source with compound (II) in the presence or absence of a liquid diluent or hydrogen halide as catalyst leads to a large extent to decomposition of compound (II).

The use of bis-1,4-cyclooctadieneNi as Ni(0)-containing starting compounds does make it possible to prepare the system comprising Ni(0) and compound (II), but this process suffers from the disadvantage of the complicated and expensive preparation of the bis-1,4-cyclooctadieneNi.

The same applies to the use of $Ni(p(O\text{-}o\text{-}C_6H_4CH_3)_3)_2$ $(C_2H_4)$ as Ni(0)-containing starting compound.

The preparation of the system comprising Ni(0) and compound (II) starting from nickel chloride and zinc as Ni(0) source is known. A disadvantage of this process is the simultaneous formation of the specified catalyst system and zinc chloride.

If the use of the pure catalyst system is envisaged, the zinc chloride firstly has to be removed before use, which is costly.

If the mixture of catalyst system and zinc chloride is used instead of the pure catalyst system, then the work-up of the mixture of exhausted catalyst system and zinc chloride poses a great problem.

A further disadvantage of the catalyst system comprising Ni(0) and compound (II) is that compound (II) can be obtained only by way of a technically complicated and expensive synthesis.

It is an object of the present invention to provide a catalyst system which can be synthesized in a technically simple and economical way and displays selectivities and activities comparable to those of a catalyst system comprising Ni(0) and compound (II), especially in the hydrocyanation of compounds having conjugated olefinic double bonds, e.g. butadiene, and of compounds having one olefinic double bond and another unsaturated group, e.g. 2-pentenenitrile, 3-pentenenitrile, 4-pentenenitrile, 2-pentenoic esters, 3-pentenoic esters or 4-pentenoic esters.

We have found that this object is achieved by the system defined at the outset and a process for its preparation.

According to the present invention, Ni(0) is used as compound a).

It is advantageous to use metallic nickel as Ni(0), in which case further elements can be alloyed with the metallic nickel. In a preferred embodiment, pure metallic nickel can be used. For the purposes of the present invention, the pure metallic nickel can contain the impurities which are usual in commercial product.

The geometric form of the metallic nickel is not critical per se. However, it has been found to be advantageous to use metallic nickel having a large surface area per unit weight so as to achieve a high reaction rate in step a) of the process of the present invention. Suitable forms of nickel are, for example, nickel sponge or preferably finely divided nickel powder. Such high surface area metallic nickel is known per se and is commercially available.

According to the present invention, compound (I) has the formula

For the purposes of the present invention, compound (I) is either a single compound or a mixture of various compounds having the abovementioned formula.

According to the present invention, $X^1, X^2, X^3$ are each, independently of one another, oxygen or a single bond.

If all of the groups $X^1, X^2$ and $X^3$ are single bonds, the compound (I) is a phosphine of the formula $P(R^1R^2R^3)$ in which $R^1, R^2$ and $R^3$ are as defined in this description.

If two of the groups $X^1, X^2$ and $X^3$ are single bonds and one is oxygen, the compound (I) is a phosphinite of the formula $P(OR^1)(R^2)(R^3)$ or $P(R^1)(OR^2)(R^3)$ or $P(R^1)(R^2)(OR^3)$ in which $R^1$, $R^2$ and $R^3$ are as defined in this description.

If one of the groups $X^1, X^2$ and $X^3$ is a single bond and two are oxygen, the compound (I) is a phosphonite of the formula $P(ORL)(OR^2)(R^3)$ or $P(R^1)(OR^2)(OR^3)$ or $P(ORL)(R^2)(OR^3)$ in which $R^1$, $R^2$ and $R^3$ are as defined in this description.

In a preferred embodiment, all of the groups $X^1, X^2$ and $X^3$ are oxygen, so that compound (I) is advantageously a phosphite of the formula $P(OR^1)(OR^2)(OR^3)$ in which $R^1$, $R^2$ and $R^3$ are as defined in this description.

According to the present invention, $R^1, R^2, R^3$ are, independently of one another, identical or different organic radicals.

Suitable radicals $R^1$, $R^2$ and $R^3$ are, independently of one another, alkyl radicals, advantageously having from 1 to 10 carbon atoms, e.g. methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, advantageously having from 1 to 20 carbon atoms, e.g. 1,1'-biphenol, 1,1'-binaphthol.

The groups $R^1$, $R^2$ and $R^3$ may be joined to one another directly, i.e. not solely via the central phosphorus atom. It is preferred that the groups $R^1$, $R^2$ and $R^3$ are not joined to one another directly.

In a preferred embodiment, the groups $R^1$, $R^2$ and $R^3$ are radicals selected from the group consisting of phenyl, o-tolyl, m-tolyl and p-tolyl.

In a particularly preferred embodiment, not more than two of the groups $R^1$, $R^2$ and $R^3$ are phenyl groups.

In another preferred embodiment, not more than two of the groups $R^1$, $R^2$ and $R^3$ are o-tolyl groups.

Particularly preferred compounds (I) are those of the formula

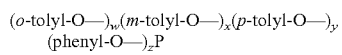

where w, x, y, z are each a natural number
and w+x+y+z=3 and
w, z are each less than or equal to 2, for example (p-tolyl-O—)(phenyl)$_2$P, (m-tolyl-O—)(phenyl)$_2$P, (o-tolyl-O—)(phenyl)$_2$P, (p-tolyl-O—)$_2$(phenyl)P, (m-tolyl-O—)$_2$(phenyl)P, (o-tolyl-O—)$_2$(phenyl)P, (m-tolyl-O—)(p-tolyl-O—)(phenyl)P, (o-tolyl-O—)(p-tolyl-O—)(phenyl)P, (o-tolyl-O—)(m-tolyl-O—)(phenyl)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—) (m-tolyl-O—)$_2$P (o-tolyl-O—)$_2$ (m-tolyl-O—)P or mixtures of such compounds.

Thus, for example, mixtures comprising (m-tolyl-O—)$_3$P, (m-tolyl-O—)$_2$(p-tolyl-O—)P, (m-tolyl-O—) (p-tolyl-O—)$_2$P and (p-tolyl-O—)$_3$P can be obtained by reacting a mixture comprising m-cresol and p-cresol, in particular in a molar ratio of 2:1, as is obtained in the refining of petroleum by distillation, with a phosphorus trihalide such as phosphorus trichloride.

Such compounds (I) and their preparation are known per se.

According to the present invention, the system has a molar ratio of compound (I) to Ni(0) in the range from 4:1 to 10:1, preferably from 4:1 to 8:1, in particular from 4:1 to 6:1.

According to the present invention, compound (II) has the formula

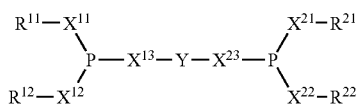

where
$X^{11}$, $X^{12}$, $X^{13}$ $X^{21}$, $X^{22}$, $X^{23}$ are each, independently of one another, oxygen or a single bond,
$R^{11}$, $R^{12}$ are identical or different, individual or bridged organic radicals,
$R^{21}$, $R^{22}$ are identical or different, individual or bridged organic radicals
Y is a bridging group.

For the purposes of the present invention, compound (II) is a single compound or a mixture of various compounds of the abovementioned formula.

In a preferred embodiment, $X^{11}$, $X^{12}$, $X^{13}$ $X^{21}$, $X^{22}$, $X^{23}$ can each be oxygen. In such a case, the bridging group Y is linked to phosphite groups.

In another preferred embodiment, $X^{11}$ and $X^{12}$ are each oxygen and $X^{13}$ is a single bond or $X^{11}$ and $X^{13}$ are each oxygen and $X^{12}$ is a single bond, so that the phosphorus atom surrounded by $X^{11}$, $X^{12}$ and $X^{13}$ is the central atom of a phosphonite. In such a case, it is possible for each of $X^{21}$, $X^{22}$ and $X^{23}$ to be oxygen or $X^{21}$ and $X^{22}$ each to be oxygen and $X^{23}$ to be a single bond or $X^{21}$ and $X^{23}$ each to be oxygen and $X^{22}$ to be a single bond or $X^{23}$ to be oxygen and $X^{21}$ and $X^{22}$ each to be a single bond or $X^{21}$ to be oxygen and $X^{22}$ and $X^{23}$ each to be a single bond or each of $X^{21}$, $X^{22}$ and $X^{23}$ to be a single bond, so that the phosphorus atom surrounded by $X^{21}$, $X^{22}$ and $X^{23}$ is the central atom of a phosphite, phosphonite, phosphinite or phosphine, preferably a phosphonite.

In another preferred embodiment, $X^{13}$ is oxygen and $X^{11}$ and $X^{12}$ are each a single bond or $X^{11}$ is oxygen and $X^{12}$ and $X^{13}$ are each a single bond, so that the phosphorus atom surrounded by $X^{11}$, $X^{12}$ and $X^{13}$ is the central atom of a phosphinite. In such a case, it is possible for each of $X^{21}$, $X^{22}$ and $X^{23}$ to be oxygen or $X^{23}$ to be oxygen and $X^{21}$ and $X^{22}$ each to be a single bond or $X^{21}$ to be oxygen and $X^{22}$ and $X^{23}$ each to be a single bond or each of $X^{21}$, $X^{22}$ and $X^{23}$ to be a single bond, so that the phosphorus atom surrounded by $X^{21}$, $X^{22}$ and $X^{23}$ is the central atom of a phosphite, phosphinite or phosphine, preferably a phosphinite.

In another preferred embodiment, $X^{11}$, $X^{12}$ and $X^{13}$ are each a single bond, so that the phosphorus atom surrounded by $X^{11}$, $X^{12}$ and $X^{13}$ is the central atom of a phosphine. In such a case, it is possible for each of $X^{21}$, $X^{22}$ and $X^{23}$ to be oxygen or each of $X^{21}$, $X^{22}$ and $X^{23}$ to be a single bond, so that the phosphorus atom surrounded by $X^{21}$, $X^{22}$ and $X^{23}$ is the central atom of a phosphite or phosphine, preferably a phosphine.

Suitable bridging groups Y are advantageously substituted, for example by $C_1$-$C_4$-alkyl, halogen such as fluorine, chlorine, bromine, halogenated alkyl such as trifluoromethyl, aryl such as phenyl, or unsubstituted aryl groups, preferably those having from 6 to 20 carbon atoms in the aromatic system, in particular pyrocatechol, bis(phenol) or bis(naphthol).

The radicals $R^{11}$ and $R^{12}$ can be identical or different organic radicals. Advantageous radicals $R^{11}$ and $R^{12}$ are aryl radicals, preferably those having from 6 to 10 carbon atoms, which may be unsubstituted or monosubstituted or polysubstituted, in particular by $C_1$-$C_4$-alkyl, halogen such as fluorine, chlorine, bromine, halogenated alkyl such as trifluoromethyl, aryl such as phenyl, or unsubstituted aryl groups.

The radicals $R^{21}$ and $R^{22}$ can be identical or different organic radicals. Advantageous radicals $R^{21}$ and $R^{22}$ are aryl radicals, preferably those having from 6 to 10 carbon atoms, which may be unsubstituted or monosubstituted or polysubstituted, in particular by $C_1$-$C_4$-alkyl, halogen such as fluorine, chlorine, bromine, halogenated alkyl such as trifluoromethyl, aryl such as phenyl, or unsubstituted aryl groups.

The radicals $R^{11}$ and $R^{12}$ may be individual or bridged. The radicals $R^{21}$ and $R^{22}$ may be individual or bridged.

It is possible for the radicals $R^{11}$, $R^{12}$, $R^{21}$ and $R^{22}$ all to be individual, for two to be bridged and two to be individual or for all four to be bridged in the manner described.

In a particularly preferred embodiment, the compounds of the formulae I, II, III, IV and V mentioned in U.S. Pat. No. 5,723,641 can be employed.

In a particularly preferred embodiment, the compounds of the formulae I, II, III, IV, V, VI and VII mentioned in U.S. Pat. No. 5,512,696, in particular the compounds used there in Examples 1 to 31, can be employed.

In a particularly preferred embodiment, the compounds of the formulae I, II, III, IV, V, VI, VII, VIII, IX, X, XI, XII, XIII, XIV and XV mentioned in U.S. Pat. No. 5,821,378, in particular the compounds used there in Examples 1 to 73, can be employed.

In a particularly preferred embodiment, the compounds of the formulae I, II, III, IV, V and VI mentioned in U.S. Pat. No. 5,512,695, in particular the compounds used there in Examples 1 to 6, can be employed.

In a particularly preferred embodiment, the compounds of the formulae I, II, III, IV, V, VI, VII, VIII, IX, X, XI, XII, XIII and XIV mentioned in U.S. Pat. No. 5,981,772, in particular the compounds used there in Examples 1 to 66, can be employed.

In a particularly preferred embodiment, the compounds mentioned in U.S. Pat. No. 6,127,567 and the compounds used there in Examples 1 to 29 can be employed.

In a particularly preferred embodiment, the compounds of the formulae I, II, III, IV, V, VI, VII, VIII, IX and X mentioned in U.S. Pat. No. 6,020,516, in particular the compounds used there in Examples 1 to 33, can be employed.

In a particularly preferred embodiment, the compounds mentioned in U.S. Pat. No. 5,959,135 and the compounds used there in Examples 1 to 13 can be employed.

In a particularly preferred embodiment, the compounds of the formulae I, II and III mentioned in U.S. Pat. No. 5,847,191 can be employed.

In a particularly preferred embodiment, the compounds mentioned in U.S. Pat. No. 5,523,453, in particular the compounds shown there in formulae 1, 2, 3, 4, 5, 6, 7, 8, 9, 10, 11, 12, 12, 13, 14, 15, 16, 17, 18, 19, 20 and 21, can be employed.

In a particularly preferred embodiment, the compounds mentioned in WO 01/14392, preferably the compounds shown there in formulae V, VI, VII, VIII, IX, X, XI, XII, XIII, XIV, XV, XVI, XVII, XXI, XXII, XXIII, can be employed.

In a particularly preferred embodiment, the compounds mentioned in WO 98/27054 can be employed.

In a particularly preferred embodiment, the compounds mentioned in WO 99/13983 can be employed.

In a particularly preferred embodiment, the compounds mentioned in WO 99/64155 can be employed.

In a particularly preferred embodiment, the compounds mentioned in the German patent application DE 10038037.9, filed on Aug. 2, 2000, can be employed.

In a particularly preferred embodiment, the compounds mentioned in the German patent application DE 10046025.9, filed on Sep. 18, 2000, can be employed.

Such compounds (II) and their preparation are known per se.

According to the present invention, the system has a molar ratio of compound (II) to Ni(0) in the range from 1:1 to 4:1, preferably from 1:1 to 3:1. In a particular embodiment, it is possible, especially in the case of compounds (II) which are difficult to prepare or are expensive, to employ a molar ratio of compound (II) to Ni(0) in the range from 1:1 to 2:1.

Compound (I) and compound (II) should advantageously be capable of forming complexes with Ni(0). In general, compound (I) has only one coordination position capable of bonding to Ni(0), while compound (II) generally has, depending on geometry, bond strength and the presence of other compounds which can coordinate to Ni(0), e.g. compound (I), one or two coordination positions capable of bonding to Ni(0).

In a preferred embodiment, the system of the present invention comprises an Ni(0) complex of the formula N1(O)(compound(I))$_x$(compound(II)), where x=1, 2.

According to the present invention, the systems can be obtained by a) reacting Ni(0) with a compound (I) in the presence of a liquid diluent to give a first system comprising Ni(0) and compound (I) and then b) reacting this first system with a compound (II) in the presence of a liquid diluent to give a system.

According to the present invention, from 4 to 10 mol, preferably from 4 to 8 mol, in particular from 4 to 6 mol, of compound (I) are used per mol of Ni(0) in step a).

In an advantageous embodiment, the liquid diluent used in step a) can be a compound of the formula (I), an olefinically unsaturated nitrile, preferably a pentenenitrile such as cis-2-pentenenitrile, trans-2-pentenenitrile, cis-3-pentenenitrile, trans-3-pentenenitrile, 4-pentenenitrile, 2-methyl-3-butenenitrile, cis-2-methyl-2-butenenitrile, trans-2-methyl-2-butenenitrile, a dinitrile such as adiponitrile, ethylglutaronitrile, an aromatic such as benzene, toluene, o-xylene, m-xylene, p-xylene, an aliphatic such as cyclohexane or a mixture of such compounds.

The preparation of the first system in step a) can advantageously be carried out in the presence of a homogeneous or heterogeneous, preferably homogeneous, catalyst.

As homogeneous catalyst, it is advantageous to use a protic acid or a mixture of such protic acids, for example hydrochloric acid.

An advantageous homogeneous catalyst is a compound of the formula

where $R^1$, $R^2$, $X^1$, $X^2$ are as defined above, or a mixture of such compounds.

The catalyst used in step a) can be carried over from step a) to step b). It has been found to be advantageous to remove the catalyst from step a) between steps a) and b).

In an advantageous embodiment, from 1 to 4 mol, preferably from 1 to 3 mol, of compound (II) are used per mol of Ni(0). In a particular embodiment, a molar ratio of compound (II) to Ni(0) in the range from 1:1 to 2:1 can be employed, especially in the case of compounds (II) which are difficult to prepare or are expensive.

In an advantageous embodiment, the liquid diluent used in step b) can be a compound of the formula (I), an olefinically unsaturated nitrile, preferably a pentenenitrile such as cis-2-pentenenitrile, trans-2-pentenenitrile, cis-3-pentenenitrile, trans-3-pentenenitrile, 4-pentenenitrile, 2-methyl-3-butenenitrile, cis-2-methyl-2-butenenitrile, trans-2-methyl-2-butenenitrile, a dinitrile such as adiponitrile, methylglutaronitrile, an aromatic such as benzene, toluene, o-xylene, m-xylene, p-xylene, an aliphatic such as cyclohexane or a mixture of such compounds.

In a particularly preferred embodiment, the same liquid diluent is used in step a) and step b).

The present invention further provides a process for preparing mixtures of monoolefinic $C_5$-mononitriles having nonconjugated C=C and C=N bonds by hydrocyanation of a 1,3-butadiene-containing hydrocarbon mixture in the presence of a catalyst comprising at least one of the above-described systems according to the present invention.

The preparation of monoolefinic $C_5$-mononitriles by the process of the present invention is preferably carried out using a hydrocarbon mixture which has a 1,3-butadiene content of at least 10% by volume, preferably at least 25% by volume, in particular at least 40% by volume.

To prepare mixtures of monoolefinic $C_5$-mononitriles which comprise, for example, 3-pentenenitrile and 2-methyl-3-butenenitrile and are suitable as intermediates for further processing to produce adiponitrile, it is possible to use pure butadiene or 1,3-butadiene-containing hydrocarbon mixtures.

1,3-Butadiene-containing hydrocarbon mixtures are available on an industrial scale. Thus, for example, the refining of petroleum by steam cracking of naphtha produces a hydrocarbon mixture known as $C_4$ fraction which has a high total olefin content of which about 40% is 1,3-butadiene and the remainder is made up of monoolefins and multiply unsaturated hydrocarbons together with alkanes. These streams always contain small proportions of generally up to 5% of alkynes, 1,2-dienes and vinylacetylene.

Pure 1,3-butadiene can be isolated from industrially available hydrocarbon mixtures by, for example, extractive distillation.

$C_4$ fractions are, if appropriate, substantially free of alkynes, e.g. propyne or butyne, of 1,2-dienes, e.g. propadiene, and of alkenynes, e.g. vinylacetylene. Otherwise, products in which a C=C double bond is conjugated with the C=N bond may be obtained. It is known from "Applied Homogeneous Catalysis with Organometalic Compounds", vol. 1, VCH Weinheim, p. 479, that the conjugated 2-pentenenitrile formed in the isomerization of 2-methyl-3-butenenitrile and 3-pentenenitrile acts as a reaction inhibitor for the second addition of hydrogen cyanide to form adiponitrile. It has been found that the above-mentioned conjugated nitrites obtained in the hydrocyanation of an unpretreated $C_4$ fraction also act as catalyst poisons for the first reaction step of the production of adipic acid, viz. the monoaddition of hydrogen cyanide.

For this reason, those components which act as catalyst poisons in catalytic hydrocyanation, in particular alkynes, 1,2-dienes and mixtures thereof, are advantageously removed completely or partially from the hydrocarbon mixture. To remove these components, the $C_4$ fraction is subjected to a catalytic partial hydrogenation prior to the addition of hydrogen cyanide. This partial hydrogenation is carried out in the presence of a hydrogenation catalyst which is capable of selectively hydrogenating alkynes and 1,2-dienes in the presence of other dienes and monoolefins.

Suitable heterogeneous catalyst systems generally comprise a transition metal compound on an inert support. Suitable inorganic supports are the oxides, in particular silicon and aluminum oxides, aluminosilicates, zeolites, carbides, nitrides, etc, customary for this purpose and mixtures thereof. Preferred supports are $Al_2O_3$, $SiO_2$ and mixtures thereof. In particular, the heterogeneous catalysts used are those described in U.S. Pat. No. 4,587,369; U.S. Pat. No. 4,704,492 and U.S. Pat. No. 4,493,906, which are hereby fully incorporated by reference. Further suitable catalyst systems based on Cu are marketed by Dow Chemical as KLP catalyst.

The addition reaction of hydrogen cyanide with 1,3-butadiene or a 1,3-butadiene-containing hydrocarbon mixture, e.g. a pretreated, partially hydrogenated $C_4$ fraction, can be carried out continuously, semicontinuously or batchwise.

In a useful variant of the process of the present invention, the addition reaction of the hydrogen cyanide is carried out continuously. Suitable reactors for the continuous reaction are known to those skilled in the art and are described, for example, in Ullmanns Enzyklopadie der technischen Chemie, vol. 1, 3rd edition, 1951, p. 743 ff. The continuous variant of the process of the present invention is preferably carried out using a cascade of stirred vessels or a tube reactor.

In a preferred variant of the process of the present invention, the addition reaction of hydrogen cyanide with 1,3-butadiene or a 1,3-butadiene-containing hydrocarbon mixture is carried out semicontinuously.

The semicontinuous process comprises:
a) charging a reactor with the hydrocarbon mixture, if desired part of the hydrogen cyanide and a hydrocyanation catalyst according to the present invention, if desired one produced in situ, and, if desired, a solvent,
b) reacting the mixture at elevated temperature and superatmospheric pressure, with hydrogen cyanide being fed in at the rate at which it is consumed,
c) completing the reaction by provision of an after-reaction time and subsequently working up the mixture.

Suitable pressure-rated reactors are known to those skilled in the art and are described, for example, in Ullmanns Enzyklopadie der technischen Chemie, vol. 1, 3rd edition, 1951, p. 769 ff. In general, the process of the present invention is carried out using an autoclave which may, if desired, be provided with a stirrer and an internal lining. For the above steps, the following procedures/conditions are preferred:

Step a):

The pressure-rated reactor is charged with the partially hydrogenated $C_4$ fraction, hydrogen cyanide, a hydrocyanation catalyst and, if desired, a solvent prior to commencement of the reaction. Suitable solvents are those mentioned above for the preparation of the catalysts of the present invention, preferably aromatic hydrocarbons such as toluene and xylene or tetrahydrofuran.

Step b):

The reaction of the mixture is generally carried out at elevated temperature and superatmospheric pressure. The reaction temperature is generally in a range from about 0 to 200° C., preferably from about 50 to 150° C. The pressure is generally in a range from about 1 to 200 bar, preferably from about 1 to 100 bar, in particular from 1 to 50 bar, particularly preferably from 1 to 20 bar. During the reaction, hydrogen cyanide is fed in at a rate corresponding to that at which it is consumed, with the pressure in the autoclave remaining essentially constant. The reaction time is from about 30 minutes to 5 hours.

Step c):

To complete the conversion, the reaction time can be followed by an after-reaction time of from 0 minutes to about 5 hours, preferably from about 1 hour to 3.5 hours, during which no more hydrogen cycanide is fed into the autoclave. The temperature during this time is kept essentially constant at the level of the reaction temperature previously set. Work-up is carried out by customary methods and comprises separating off the unreacted 1,3-butadiene and the unreacted hydrogen cyanide, e.g. by scrubbing or extraction, and working up the remaining reaction mixture by distillation to separate off the desired product and to recover the still active catalyst.

In a further useful variant of the process of the present invention, the addition reaction of the hydrogen cyanide with the 1,3-butadiene-containing hydrocarbon mixture is carried out batchwise. Here, the reaction conditions employed are essentially those described for the semicontinuous process, but no additional hydrogen cyanide is fed in in step b); all the hydrogen cycanide for the reaction is present in the initial charge.

In general, the preparation of adiponitrile from a butadiene-containing mixture by addition of 2 molar equivalents of hydrogen cyanide can be subdivided into three steps:

1. Preparation of $C_5$-monoolefin mixtures having a nitrile function.
2. Isomerization of the 2-methyl-3-butenenitrile present in these mixtures to form 3-pentenenitrile and isomerization of the 3-pentenenitrile formed in this way and that already present in the mixture from step 1 to form various n-pentenenitriles. Here, a very high proportion of 3-pentenenitrile or 4-pentenenitrile and a very low proportion of conjugated 2-pentenenitrile and 2-methyl-2-butenenitrile, which may act as catalyst poisons, should be formed.
3. Preparation of adiponitrile by addition of hydrogen cyanide onto the 3-pentenenitrile which has been formed in step 2 and is isomerized beforehand "in situ" to 4-pentenenitrile. By-products which occur are, for example, 2-methylglutaronitrile from the Markovnikov addition of hydrogen cyanide onto 4-pentenenitrile or the anti-Markovnikov addition of hydrogen cyanide onto 3-pentenenitrile and ethylsuccinonitrile from the Markovnikov addition of hydrogen cyanide onto 3-pentenenitrile.

Advantageously, the catalysts of the present invention based on phosphonite ligands are also suitable for the structural isomerization and double bond isomerization in step 2 and/or the second addition of hydrogen cyanide in step 3.

In a useful embodiment of the process of the present invention, the ratio of 3-pentenenitrile to 2-methyl-3-butenenitrile obtained in the monoaddition reaction of hydrogen cyanide with the 1,3-butadiene-containing hydrocarbon mixture is at least 1.9:1, preferably at least 2.1:1.

Advantageously, the catalysts used according to the present invention not only display a high selectivity to the monoaddition products obtained in the hydrocyanation of 1,3-butadiene-containing hydrocarbon mixtures but they can also be admixed with an excess of hydrogen cyanide in the hydrocyanation without appreciable precipitation of inactive nickel(II) compounds, e.g. nickel(II) cyanide, occurring. In contrast to known hydrocyanation catalysts based on uncomplexed phosphine and phosphite ligands, the catalysts of the formula I are thus suitable not only for continuous hydrocyanation processes in which an excess of hydrogen cyanide in the reaction mixture can generally be effectively avoided but also for semicontinuous processes and batch processes in which a large excess of hydrogen cyanide is generally present. Thus, the catalysts used according to the present invention and the hydrocyanation processes based on them generally allow greater recirculation of catalysts and display longer catalyst operating lives than do known processes. This is advantageous both in terms of improved economics and also from an ecological point of view, since the nickel cyanide formed from the active catalyst by reaction with hydrogen cyanide is highly toxic and has to be worked up or disposed of, which is very costly.

Apart from the hydrocyanation of 1,3-butadiene-containing hydrocarbon mixtures, the systems of the present invention are generally suitable for all customary hydrocyanation processes. Particular mention may be made of the hydrocyanation of nonactivated olefins, e.g. styrene and 3-pentenenitrile.

A further advantageous embodiment of hydrocyanation and isomerization can be derived from U.S. Pat. No. 6,981,772, whose contents are hereby incorporated by reference, with the proviso that a catalyst system according to the present invention or a mixture of such systems is used in place of the catalysts mentioned in that patent.

A further advantageous embodiment of hydrocyanation and isomerization can be derived from U.S. Pat. No. 6,127,567, whose contents are hereby incorporated by reference, with the proviso that a catalyst system according to the present invention or a mixture of such systems is used in place of the catalysts mentioned in that patent.

A further advantageous embodiment of a hydrocyanation process can be derived from U.S. Pat. No. 5,693,843, whose contents are hereby incorporated by reference, with the proviso that a catalyst system according to the present invention or a mixture of such systems is used in place of the catalysts mentioned in that patent.

A further advantageous embodiment of a hydrocyanation process can be derived from U.S. Pat. No. 5,523,453, whose contents are hereby incorporated by reference, with the proviso that a catalyst system according to the present invention or a mixture of such systems is used in place of the catalysts mentioned in that patent.

The invention is illustrated by the following nonlimiting examples.

EXAMPLES

The yields were determined by gas chromatography (column: 30 m Stabil-Wachs, temperature program: 5 minutes isothermal at 50° C., then heating at a rate of 5° C./min to 240° C., gas chromatography: Hewlett Packard HP 5890)

All examples were carried out under a protective argon atmosphere.

The abbreviation nickel(0)-(m/p-tolyl phosphite) refers to a mixture comprising 2.35% by weight of Ni(0), 19% by weight of 3-pentenenitrile and 78.65% by weight of m/p-tolyl phosphite having an m:p ratio of 2:1.

Chelating ligands used were:

Ligand 1

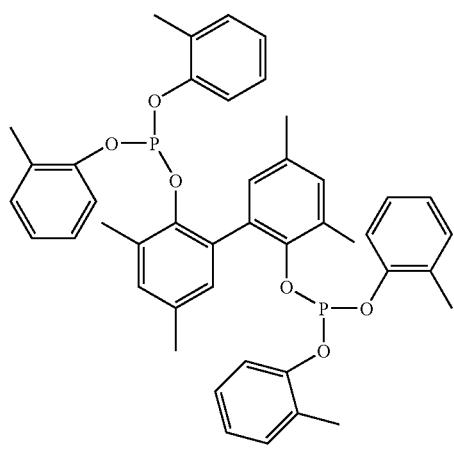

Ligand 2

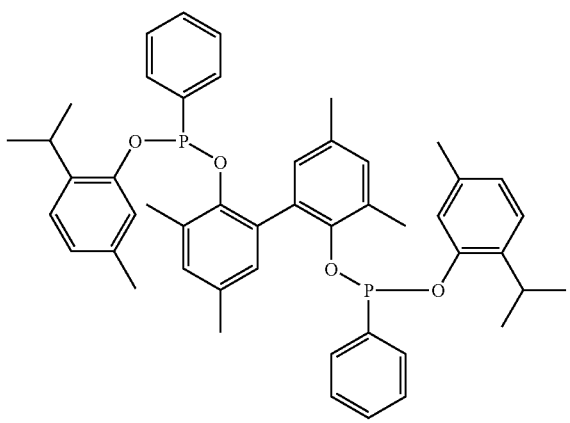

Ligand 3

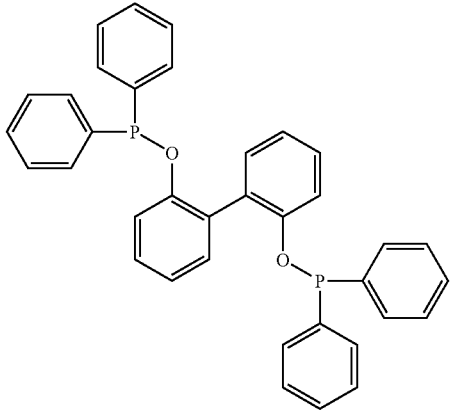

Ni(COD)$_2$ is bis(1,4-cyclooctadiene)Ni(0).

In the tables, 2M3BN is 2-methyl-3-butenenitrile, t2M2BN is trans-2-methyl-2-butenenitrile, c2M2BN is cis-2-methyl-2-butenenitrile, t2PN is trans-2-pentenenitrile, 4PN is 4-pentenenitrile, t3PN is trans-3-pentenenitrile, c3PN is cis-3-pentenenitrile, MGN is methylglutaronitrile and ADN is adiponitrile.

Examples 1-18

Use of Ligand 1 as Compound (II)

Examples 1-3

Isomerization of 2-methyl-3-butenenitrile to 3-pentenenitrile

Example 1

Comparison 1 molar equivalent of Ni(0)-(m/p-tolyl phosphite) (0.5 mmol of Ni(0)) was admixed with 465 molar equivalents of 2-methyl-3-butenenitrile and the mixture was heated to 115° C. Samples were taken from the reaction mixture after 90 minutes and after 180 minutes and the following yields (in percent) were determined:

| Time | 2M3BN | t2M2BN | c2M2BN | t2PN | 4PN | t3PN | c3PN | 3PN/2M3BN |
|---|---|---|---|---|---|---|---|---|
| 90 min | 84.5 | 1.3 | 0.3 | | | 13.0 | | 0.15 |
| 180 min | 72.4 | 1.5 | 0.5 | | | 24.4 | | 0.34 |

Example 2

Comparison 1 molar equivalent of Ni(COD)$_2$ (0.58 mmol of Ni(0)) was admixed with 3 molar equivalents of ligand 1 and 465 molar equivalents of 2-methyl-3-butenenitrile, the mixture was stirred at 25° C. for 1 hour and then heated to 115° C. Samples were taken from the reaction mixture after 90 minutes and after 180 minutes and the following yields (in percent) were determined:

| Time | 2M3BN | t2M2BN | c2M2BN | t2PN | 4PN | t3PN | c3PN | 3PN/2M3BN |
|---|---|---|---|---|---|---|---|---|
| 90 min | 4.69 | 1.4 | 0.22 | 0.3 | 0.78 | 87.82 | 4.80 | 19.74 |
| 180 min | 4.52 | 1.34 | 0.16 | 0.23 | 1.41 | 85.3 | 7.0 | 20.42 |

Example 3

According to the Present Invention 1 molar equivalent of Ni(0)-(m/p-tolyl phosphite) (0.4 mmol of Ni(0)) was admixed with 1 molar equivalent of ligand 1 and 465 molar equivalents of 2-methyl-3-butenenitrile, the mixture was stirred at 25° C. for 12 hours and then heated to 115° C. Samples were taken from the reaction mixture after 90 minutes and after 180 minutes and the following yields (in percent) were determined:

| Time | 2M3BN | T2M2BN | c2M2BN | t2PN | 4PN | T3PN | c3PN | 3PN/2M3BN |
|---|---|---|---|---|---|---|---|---|
| 90 min | 28.81 | 1.5 | | | 0.1 | 57.6 | | 2 |
| 180 min | 13.31 | 1.3 | | | 0.1 | 75.5 | | 5.68 |

Examples 4-15

Hydrocyanation of 3-pentenenitrile to adiponitrile

Example 4

Comparison 1 molar equivalent of nickel(0)-(m/p-tolyl phosphite) (0.6 mmol of Ni(0)) was admixed with 365 molar equivalents of 3-pentenenitrile, the mixture was stirred at 25° C. for 1 hour and heated to 70° C. 1 molar equivalent of ZnCl$_2$ was added to this mixture and the mixture was stirred for a further 5 minutes. 94 molar equivalents of HCN/hour*Ni in an argon carrier gas stream were passed in. Samples were taken after 30 minutes, 60 minutes and 150 minutes and the following yields (in percent) were determined:

| Time | MGN | ADN | ADN selectivity (%) |
|---|---|---|---|
| 30 min | 3.35 | 10.75 | 76.2 |
| 60 min | 6.87 | 26.39 | 79.3 |
| 150 min | 7.11 | 27.82 | 79.6 |

Example 5

Comparison

The procedure of Example 4 was repeated using 1 molar equivalent of Ni(COD)$_2$ (0.27 mmol of Ni(0)) and 1 molar equivalent of ligand 1 in place of 1 molar equivalent of nickel(0)-(m/p-tolyl phosphite).

Samples were taken after 30 minutes, 60 minutes and 150 minutes and the following yields (in percent) were determined:

| Time | MGN | ADN | ADN selectivity (%) |
|---|---|---|---|
| 30 min | 0.68 | 2.19 | 76.2 |
| 60 min | 0.99 | 6.17 | 86.2 |
| 150 min | 1.01 | 7.28 | 87.8 |

Example 6

Comparison

The procedure of Example 5 (using 0.64 mmol of Ni(0)) was repeated, except that only 38 molar equivalents of HCN/hour*Ni were passed in instead of 94 molar equivalents of HCN/hour*Ni. Samples were taken after 30 minutes, 60 minutes and 150 minutes and the following yields (in percent) were determined:

| Time | MGN | ADN | ADN selectivity (%) |
|---|---|---|---|
| 30 min | 0.88 | 1.33 | 60.0 |
| 60 min | 1.71 | 8.69 | 83.5 |
| 150 min | 2.01 | 15.90 | 88.7 |

Example 7

According to the Present Invention 1 molar equivalent of Ni(COD)$_2$ (0.61 mmol of Ni(0)) was admixed with 1 molar equivalent of ligand 1, 4 molar equivalents of m/p-tolyl phosphite (m:p=2:1) and 365 molar equivalents of 3-pentenenitrile, the mixture was stirred at 25° C. for 1 hour and heated to 70° C. 1 molar equivalent of ZnCl$_2$ was added to this mixture and the mixture was stirred for a further 5 minutes. 133 molar equivalents of HCN/hour*Ni in an argon carrier gas stream were passed in.

Samples were taken after 30 minutes, 60 minutes and 150 minutes and the following yields (in percent) were determined:

| Time | MGN | ADN | ADN selectivity (%) |
|---|---|---|---|
| 30 min | 2.86 | 17.50 | 85.9 |
| 60 min | 3.96 | 36.86 | 90.3 |
| 150 min | 6.88 | 77.27 | 91.8 |

Example 8

According to the Present Invention

The procedure of Example 7 was repeated (using 0.53 mmol of Ni(0)), except that 28 molar equivalents of HCN/hour*Ni were passed in instead of 133 molar equivalents of HCN/hour*Ni.

Samples were taken after 30 minutes, 60 minutes and 150 minutes and the following yields (in percent) were determined:

| Time | MGN | ADN | ADN selectivity (%) |
|---|---|---|---|
| 30 min | 0.49 | 8.02 | 94.2 |
| 60 min | 1.10 | 19.73 | 94.7 |
| 150 min | 1.88 | 33.54 | 94.7 |

Example 9

According to the Present Invention 1 molar equivalent of nickel(0)-(m-/p-tolyl phosphite) (0.6 mmol of Ni(0)) was admixed with 1.2 molar equivalents of ligand 1 and 365 molar equivalents of 3-pentenenitrile, the mixture was stirred at 25° C. for 12 hours and heated to 70° C. 1 molar equivalent of ZnCl$_2$ was added to this mixture and the mixture was stirred for a further 5 minutes. 131 molar equivalents of HCN/h*Ni in an Ar carrier gas stream were then passed in.

Samples were taken after 30 minutes, 60 minutes and 120 minutes and the following yields (in percent) were determined:

| Time | MGN | ADN | ADN selectivity (%) |
|---|---|---|---|
| 30 min | 1.67 | 15.21 | 90.1 |
| 60 min | 3.13 | 39.05 | 92.6 |
| 120 min | 5.15 | 65.04 | 92.7 |

Example 10

Comparison 1 molar equivalent of Ni(COD)$_2$ (0.49 mmol of Ni(0)) was admixed with 3 molar equivalents of ligand 1 and 365 molar equivalents of 3-pentenenitrile, the mixture was stirred at 25° C. for 1 hour and heated to 70° C. 1 molar equivalent of ZnCl$_2$ was added to this mixture and the mixture was stirred for a further 5 minutes. 43 molar equivalents of HCN/h*Ni in an Ar carrier gas stream were then passed in.

Samples were taken after 60 minutes and 120 minutes and the following yields (in percent) were determined:

| Time | MGN | ADN | ADN selectivity (%) |
|---|---|---|---|
| 60 min | 2.41 | 11.73 | 83.0 |
| 120 min | 3.21 | 29.14 | 90.1 |

Example 11

Comparison

The procedure of Example 10 was repeated (using 0.58 mmol of Ni(0)), except that 95 molar equivalents of HCN/h*Ni were passed in instead of 43 molar equivalents of HCN/h*Ni.

Samples were taken after 30 minutes, 60 minutes and 120 minutes and the following yields (in percent) were determined:

| Time | MGN | ADN | ADN selectivity (%) |
|---|---|---|---|
| 30 min | 1.40 | 13.32 | 90.5 |
| 160 min | 2.26 | 31.96 | 93.4 |
| 120 min | 3.69 | 58.46 | 94.0 |

Example 12

Comparison

The procedure of Example 10 was repeated (using 0.58 mmol of Ni(0)), except that the catalyst mixture was stirred at 25° C. for 12 hours instead of 1 hour and 122 molar equivalents of HCN/h*Ni were passed in instead of 43 molar equivalents of HCN/h*Ni.

Samples were taken after 30 minutes, 60 minutes and 180 minutes and the following yields (in percent) were determined:

| Time | MGN | ADN | ADN selectivity (%) |
|---|---|---|---|
| 30 min | 1.71 | 18.50 | 91.5 |
| 60 min | 2.52 | 36.10 | 93.5 |
| 180 min | 5.92 | 91.04 | 93.9 |

Example 13

Comparison

The procedure of Example 12 was repeated (using 0.4 mmol of Ni(0)), except that 150 molar equivalents of HCN/h*Ni were passed in instead of 43 molar equivalents of HCN/h*Ni.

Samples were taken after 30 minutes, 60 minutes and 120 minutes and the following yields (in percent) were determined:

| Time | MGN | ADN | ADN selectivity (%) |
|---|---|---|---|
| 30 min | 3.47 | 42.03 | 92.4 |
| 60 min | 4.90 | 67.36 | 93.2 |
| 120 min | 5.96 | 83.92 | 93.4 |

Example 14

According to the Present Invention 1 molar equivalent of nickel(0)-(m-/p-tolyl phosphite) (0.6 mmol of Ni(0)) was admixed with 3 molar equivalents of ligand 1 and 365 molar equivalents of 3-pentenenitrile, the mixture was stirred at 25° C. for 12 hours and heated to 70° C. 1 molar equivalent of $ZnCl_2$ was added to this mixture and the mixture was stirred for a further 5 minutes. 111 molar equivalents of HCN/h*Ni in an Ar carrier gas stream were then passed in.

Samples were taken after 30 minutes, 60 minutes and 120 minutes and the following yields (in percent) were determined:

| Time | MGN | ADN | ADN selectivity (%) |
|---|---|---|---|
| 30 min | 1.11 | 16.31 | 93.6 |
| 60 min | 2.11 | 36.31 | 94.5 |
| 120 min | 4.14 | 70.50 | 94.5 |

Example 15

According to the Present Invention

The procedure of Example 14 (using 0.6 mmol of Ni(0)) was repeated, except that 109 molar equivalents of HCN/h*Ni were passed in instead of 111 molar equivalents of HCN/h*Ni. Samples were taken after 30 minutes, 60 minutes and 120 minutes and the following yields (in percent) were determined:

| Time | MGN | ADN | ADN selectivity (%) |
|---|---|---|---|
| 30 min | 1.03 | 15.79 | 93.9 |
| 60 min | 2.00 | 34.31 | 94.5 |
| 120 min | 4.58 | 77.68 | 94.4 |

Examples 16-18

Hydrocyanation of 1,3-butadiene to 3-pentenenitrile

Example 16

Comparison 1 molar equivalent of nickel(0)-(m-/p-tolyl phosphite) (1 mmol of Ni(0)) was admixed with 500 molar equivalents of 1,3-butadiene and 420 molar equivalents of HCN in THF, and the mixture was placed in a glass autoclave at 25° C. and heated to 80° C.

By means of an internal thermometer, the following temperatures ere measured as a function of time during the reaction (slightly exothermic reaction):

| Time | Internal temperature |
|---|---|
| 30 min | 80.3 |
| 50 min | 80.5 |
| 60 min | 80.4 |
| 180 min | 80.3 |

After 180 minutes, the HCN conversion into 2-methyl-3-butenenitrile and 3-pentenenitrile was 9.8%. The molar ratio of 2-methyl-3-butenenitrile to 3-pentenenitrile was 1/3.4.

Example 17

Comparison 1 molar equivalent of $Ni(COD)_2$ (0.32 mmol of Ni(0)) was stirred with 3 molar equivalents of ligand 1 in THF for 20 minutes. This solution was admixed with 696 molar equivalents of 1,3-butadiene and 580 molar equivalents of HCN in THF, and the mixture was placed in a glass autoclave at 25° C. and heated to 80° C.

By means of an internal thermometer, the following temperatures were measured as a function of time during the reaction (slightly exothermic reaction):

| Time | Internal temperature |
|---|---|
| 30 min | 81.9 |
| 45 min | 82 |
| 60 min | 81.9 |
| 90 min | 81.3 |
| 180 min | 80.8 |

After 180 minutes, the HCN conversion into 2-methyl-3-butenenitrile and 3-pentenenitrile was 94.4%. The molar ratio of 2-methyl-3-butenenitrile to 3-pentenenitrile was 1/1.3.

Example 18

According to the Present Invention 1 molar equivalent of nickel(0)-(m-/p-tolyl phosphite) (1 mmol of Ni(0)) was stirred with 1.2 molar equivalents of ligand 1 in THF for 12 hours. This solution was admixed with 480 molar equivalents of 1,3-butadiene and 400 molar equivalents of HCN in THF, and the mixture was placed in a glass autoclave at 25° C. and heated to 80° C.

By means of an internal thermometer, the following temperatures were measured as a function of time during the reaction (slightly exothermic reaction):

| Time | Internal temperature |
|---|---|
| 30 min | 86 |
| 45 min | 88.6 |
| 60 min | 86.9 |
| 120 min | 80 |

After 180 minutes, the HCN conversion into 2-methyl-3-butenenitrile and 3-pentenenitrile was above 99%. The molar ratio of 2-methyl-3-butenenitrile to 3-pentenenitrile was 1/1.5.

Examples 19-25

Use of Ligand 2 as Compound (II)

Examples 19-20

Isomerization of 2-methyl-3-butenenitrile to 3-pentenenitrile

Example 19

Comparison 1 molar equivalent of Ni(COD)$_2$ (0.58 mmol of Ni(0)) was admixed with 3 molar equivalents of ligand 2 and 465 molar equivalents of 2-methyl-3-butenenitrile, the mixture was stirred at 25° C. for 1 hour and then heated to 115° C.

Samples were taken from the reaction mixture after 90 minutes and after 180 minutes and the following yields (in percent) were determined:

| Time | 2M3BN | t2M2BN | c2M2BN | t2PN | 4PN | t3PN | c3PN | 3PN/2M3BN |
|---|---|---|---|---|---|---|---|---|
| 90 min | 11.96 | 1.81 | 0.30 | 0.27 | | 82.75 | 2.48 | |
| 180 min | 4.77 | 1.81 | 0.33 | 0.18 | 1.32 | 86.6 | 4.88 | |

Example 20

According to the Present Invention 1 molar equivalent of Ni(0)-(m/p-tolyl phosphite) (0.4 mmol of Ni(0)) was admixed with 1 molar equivalent of ligand 2 and 465 molar equivalents of 2-methyl-3-butenenitrile, the mixture was stirred at 25° C. for 12 hours and heated to 115° C.

Samples were taken from the reaction mixture after 90 minutes and after 180 minutes and the following yields (in percent) were determined:

| Time | 2M3BN | t2M2BN | c2M2BN | t2PN | 4PN | t3PN | c3PN | 3PN/2M3BN |
|---|---|---|---|---|---|---|---|---|
| 90 min | 59.96 | 1.78 | | 0.32 | 0.1 | 26.45 | | 0.44 |
| 180 min | 44.09 | 2.30 | | 0.36 | 0.1 | 40.84 | | 0.93 |

Examples 21-23

Hydrocyanation of 3-pentenenitrile to adipodinitrile

Example 21

Comparison 1 molar equivalent of Ni(COD)$_2$ (0.55 mmol of Ni(0)) was admixed with 3 molar equivalents of ligand 2 and 365 molar equivalents of 3-pentenenitrile, the mixture was stirred at 25° C. for one hour and heated to 70° C. 1 molar equivalent of ZnCl$_2$ was added to this mixture and the mixture was stirred for a further 5 minutes. 142 molar equivalents of HCN/h*Ni in an Ar carrier gas stream were then passed in.

Samples were taken after 30 minutes and 60 minutes and the following yields (in percent) were determined:

| Time | MGN | ADN | ADN selectivity (%) |
|---|---|---|---|
| 30 min | 1.80 | 18.91 | 91.3 |
| 60 min | 2.51 | 32.57 | 92.9 |

Example 22

According to the Present Invention 1 molar equivalent of Ni(COD)$_2$ (0.49 mmol of Ni(0)) was admixed with 1.2 molar equivalents of ligand 2, 4 molar equivalents of m-/p-tolyl phosphite (m/p=2:1) and 365 molar equivalents of 3-pentenenitrile, the mixture was stirred at 25° C. for one hour and heated to 70° C. 1 molar equivalent of ZnCl$_2$ was added to this mixture and the mixture was stirred for a further 5 minutes. 125 molar equivalents of HCN/h*Ni in an Ar carrier gas stream were then passed in.

Samples were taken after 45 minutes and 60 minutes and the following yields (in percent) were determined:

| Time | MGN | ADN | ADN selectivity (%) |
|---|---|---|---|
| 45 min | 1.85 | 21.51 | 92.1 |
| 60 min | 2.29 | 27.58 | 92.3 |

Example 23

According to the Present Invention 1 molar equivalent of nickel(0)-(m-/p-tolyl phosphite) (0.6 mmol of Ni(0)) was admixed with 1 molar equivalent of ligand 2 and 365 molar equivalents of 3-pentenenitrile, the mixture was stirred at 25° C. for 12 hours and heated to 70° C. 1 molar equivalent of ZnCl$_2$ was added to this mixture and the mixture was stirred for a further 5 minutes. 120 molar equivalents of HCN/h*Ni in an Ar carrier gas stream were then passed in.

Samples were taken after 30 minutes and 60 minutes and the following yields (in percent) were determined:

| Time | MGN | ADN | ADN selectivity (%) |
|---|---|---|---|
| 30 min | 1.22 | 11.49 | 90.4 |
| 60 min | 2.88 | 26.12 | 90.0 |

Examples 24-25

Hydrocyanation of 1,3-butadiene to 3-pentenenitrile

Example 24

Comparison 1 molar equivalent of Ni(COD)$_2$ (1 mmol of Ni(0)) was stirred with 3 molar equivalents of ligand 2 in THF for 20 minutes. This solution was admixed with 557 molar equivalents of 1,3-butadiene and 433 molar equivalents of HCN in THF, and the mixture was placed in a glass autoclave at 25° C. and heated to 80° C.

By means of an internal thermometer, the following temperatures were measured as a function of time during the reaction (slightly exothermic reaction):

| Time | Internal temperature |
|---|---|
| 15 min | 82.2 |
| 30 min | 82.1 |
| 120 min | 81.1 |

After 180 minutes, the HCN conversion into 2-methyl-3-butenenitrile and 3-pentenenitrile was 97.5%. The molar ratio of 2-methyl-3-butenenitrile to 3-pentenenitrile was 1.5/1.

Example 25

According to the Present Invention 1 molar equivalent of nickel(0)-(m-/p-tolyl phosphite) (1 mmol of Ni(0)) was stirred with 1.2 molar equivalents of ligand 2 in THF for 12 hours. This solution was admixed with 480 molar equivalents of 1,3-butadiene and 400 molar equivalents of HCN in THF, and the mixture was placed in a glass autoclave at 25° C. and heated to 80° C.

By means of an internal thermometer, the following temperatures were measured as a function of time during the reaction (slightly exothermic reaction):

| Time | Internal temperature |
|---|---|
| 30 min | 83.6 |
| 60 min | 84.6 |
| 120 min | 84.4 |
| 180 Min | 80.5 |

After 180 minutes, the HCN conversion into 2-methyl-3-butenenitrile and 3-pentenenitrile was above 99%. The molar ratio of 2-methyl-3-butenenitrile to 3-pentenenitrile was 1.35/1.

Examples 26-28

Use of Ligand 3 as Compound (II)

Example 26

Comparison 1 molar equivalent of Ni(COD)$_2$ (1 mmol of Ni(0)) was stirred with 1.2 molar equivalents of ligand 3 in THF for 20 minutes. This solution was admixed with 480 molar equivalents of 1,3-butadiene and 400 molar equivalents of HCN in THF, and the mixture was placed in a glass autoclave at 25° C. and heated to 80° C.

By means of an internal thermometer, the following temperatures were measured as a function of time during the reaction (slightly exothermic reaction):

| Time | Internal temperature |
|---|---|
| 5 min | 85 |
| 10 min | 89 |
| 15 min | 92.9 |
| 20 min | 90.3 |
| 30 min | 86.1 |
| 60 min | 82 |
| 120 min | 81 |

After 180 minutes, the HCN conversion into 2-methyl-3-butenenitrile and 3-pentenenitrile was 88.0%. The molar ratio of 2-methyl-3-butenenitrile to 3-pentenenitrile was 3/1.

Example 27

According to the Present Invention 1 molar equivalent of nickel(0)-(m-/p-tolyl phosphite) (1 mmol of Ni(0)) was stirred with 1.2 molar equivalents of ligand 3 in THF for 12 hours. This solution was admixed with 462 molar equivalents of 1,3-butadiene and 390 molar equivalents of HCN in THF, and the mixture was placed in a glass autoclave at 25° C. and heated to 80° C.

By means of an internal thermometer, the following temperatures were measured as a function of time during the reaction (slightly exothermic reaction):

| Time | Internal temperature |
|---|---|
| 30 min | 91 |
| 40 min | 122 |
| 50 min | 84 |
| 60 min | 80.2 |
| 120 min | 80.2 |

After 180 minutes, the HCN conversion into 2-methyl-3-butenenitrile and 3-pentenenitrile was above 99%. The molar ratio of 2-methyl-3-butenenitrile to 3-pentenenitrile was 2.5/1.

Example 28

According to the Present Invention

The procedure of Example 27 (using 1 mmol of Ni(0)) was repeated, except that 720 molar equivalents of 1,3-butadiene and 600 molar equivalents of HCN were used instead of 462 molar equivalents of 1,3-butadiene and 390 molar equivalents of HCN.

By means of an internal thermometer, the following temperatures were measured as a function of time during the reaction (slightly exothermic reaction):

| Time | Internal temperature |
|---|---|
| 25 min | 84 |
| 45 min | 89.1 |
| 65 min | 90.5 |
| 80 min | 80.5 |
| 120 min | 80.2 |

After 180 minutes, the HCN conversion into 2-methyl-3-butenenitrile and 3-pentenenitrile was 96/6%. The molar ratio of 2-methyl-3-butenenitrile to 3-pentenenitrile was 2.8/1.

We claim:

1. A system comprising
    a) Ni(0)
    b) from 4 to 10 mol per mol of Ni(0) in a) of a compound (I) of the formula $(o\text{-Tolyl-O})_w(m\text{-Tolyl-O})_x(p\text{-Tolyl-O}-)_y$
    $(\text{Phenyl-O}-)_z P$ where
    w, x, y, z are each a natural number and
    w+x+y+z=3 and
    w, z are each less than or equal to 2,
    and
    c) from 1 to 4 mol per mol of Ni(0) in a) of a compound (II) of the formula $$\begin{array}{c} R^{11}-X^{11} \\ \phantom{R^{11}-}\diagdown \\ \phantom{R^{11}-X^{11}}P-X^{13}-Y-X^{23}-P \\ \phantom{R^{11}-}\diagup \\ R^{12}-X^{12} \end{array} \begin{array}{c} X^{21}-R^{21} \\ \diagup \\ \\ \diagdown \\ X^{22}-R^{22} \end{array}$$

where
    $X^{11}$, $X^{12}$, $X^{13}$, $X^{21}$, $X^{22}$, $X^{23}$ are each oxygen,
    $R^{11}$, $R^{12}$ are identical or different, phenyl radicals which are unsubstituted or mono- or polysubstituted by $C_1$-$C_4$-alkyl,
    $R^{21}$, $R^{22}$ are identical or different, phenyl radicals which are unsubstituted or mono- or polysubstituted by $C_1$-$C_4$-alkyl, and
    Y is a substituted or unsubstituted pyrocatechol, bis(phenol) or bis(naphthol) group,
    which is suitable as a catalyst.

2. A system as claimed in claim 1, wherein the number of phenyl groups in compound (I) is not more than 2 and the number of o-tolyl groups in compound (I) is not more than 2.

3. A system as claimed in claim 1, comprising an Ni(0) complex of the formula

Ni(0)(compound (I))$_x$(compound (II))

where x=1, 2.

4. A process for preparing a system as defined in claim 1, which comprises
    a) reacting Ni(0) with a compound (I) in the presence of a liquid diluent to give a first system comprising Ni(0) and the compound (I) and then
    b) reacting this first system with a compound (II) in the presence of a liquid diluent to give the system as claimed in claim 1.

5. A process as claimed in claim 4, wherein metallic nickel is used as Ni(0) in step a).

6. A process as claimed in claim 4, wherein from 4 to 10 mol of compound (I) are used per mol Ni(0) in step a).

7. A process as claimed in claim 4, wherein the liquid diluent used in step a) is a compound of the formula (I), 3-pentenenitrile, 4-pentenenitrile, 2-methyl-3-butenenitrile, adiponitrile, methylglutaronitrile, an aromatic, an aliphatic or a mixture thereof.

8. A process as claimed in claim 4, wherein the preparation of the first system in step a) is carried out in the presence of a catalyst.

9. A process as claimed in claim 4, wherein the preparation of the first system in step a) is carried out in the presence of a homogeneous catalyst.

10. A process as claimed in claim 4, wherein the preparation of the first system in step a) is carried out in the presence of a protic acid as homogeneous catalyst.

11. A process as claimed in claim 4, wherein the preparation of the first system in step a) is carried out in the presence of hydrogen chloride as homogeneous catalyst.

12. A process as claimed in claim 4, wherein the preparation of the first system in step a) is carried out in the presence of a compound of the formula $(R^1X^1)(R^2X^2)PCl$ or $(R^1X^1)PCl_2$, where
    $X^1$, $X^2$ are each oxygen, and
    $R^1$, $R^2$ are each, independently of one another, a phenyl, o-tolyl, m-tolyl or p-tolyl group,
    as homogeneous catalyst.

13. A process as claimed in claim 4, wherein the catalyst is removed between step a) and step b).

14. A process as claimed in claim 4, wherein from 1 to 4 mol of compound (II) are used per mol Ni(0) in step b).

15. A process as claimed in claim 4, wherein the liquid diluent used in step b) is a compound of the formula (I), 3-pentenenitrile, 4-pentenenitrile, 2-methyl-3-butenenitrile, adiponitrile, methylglutaronitrile, an aromatic, an aliphatic or a mixture thereof.

16. A process as claimed in claim 4, wherein the same liquid diluent is used in step a) and in step b).

* * * * *